United States Patent

Clarén

[11] Patent Number: 5,260,692
[45] Date of Patent: Nov. 9, 1993

[54] CONTROL DEVICE FOR FLUID CONTAINERS OF FLEXIBLE MATERIAL

[75] Inventor: Jan Clarén, Lund, Sweden

[73] Assignee: Crafcontrol AB, Lund, Sweden

[21] Appl. No.: 768,552

[22] PCT Filed: Mar. 27, 1990

[86] PCT No.: PCT/SE90/00092
 § 371 Date: Nov. 12, 1991
 § 102(e) Date: Nov. 12, 1991

[87] PCT Pub. No.: WO90/11501
 PCT Pub. Date: Oct. 4, 1990

[30] Foreign Application Priority Data
Mar. 28, 1989 [SE] Sweden .................. 8901055

[51] Int. Cl.⁵ ............................. G01B 21/00
[52] U.S. Cl. ........................ 340/614; 73/726; 73/731; 338/4
[58] Field of Search .......... 340/450, 612, 614, 618; 73/731, 727, 726, 720, 721; 128/DIG. 13, 886; 338/4

[56] References Cited

U.S. PATENT DOCUMENTS

| 2,420,148 | 5/1947 | Ostergren | 73/731 |
| 2,715,666 | 8/1955 | Stinchfield | 73/770 |
| 3,546,944 | 12/1970 | Mack | 73/731 |
| 5,121,107 | 6/1992 | Newell | 340/618 |

FOREIGN PATENT DOCUMENTS 0130670 1/1985 European Pat. Off. .

Primary Examiner—Donald O. Woodreil
Attorney, Agent, or Firm—Jacobson, Price, Holman & Stern

[57] ABSTRACT

A control device for fluid containers (16) of a flexible material, particularly for controlling the level of stomi bags, comprises an elastic resistance element (10) having an electric resistance which changes by stretching of the element, which is adapted to be fixedly connected with the container wall at the ends thereof to extend over an extensible portion (17) of the container wall. Means (12) are provided for connecting an alarm means (19) reacting to a change in the resistance of the resistance element.

5 Claims, 2 Drawing Sheets

CONTROL DEVICE FOR FLUID CONTAINERS OF FLEXIBLE MATERIAL

BACKGROUND OF THE INVENTION

Field of the Invention

The invention relates to a stomi bag.

Description of the Related Art

A problem for many stomi patients is that the stomi bag will be too full and will loosen, which easily occurs in the night when the patient is asleep and therefore has no control over the stomi bag. Due to the stomi bag coming loose the contents thereof partly can flow out and cause inconvenience. Accordingly, there is a pressing demand for an effective and reliable control device which in one manner or the other can indicate that the stomi bag has reached such a level that it should be emptied.

As a container of flexible material is being filled with a fluid, the pressure against the wall of the container will increase, and according to U.S. Pat. No. 3,546,944 there has already been proposed a device which senses said pressure. According to said publication a member is provided over a fold of the container wall and is connected to the wall at both sides of the fold. When a predetermined pressure has been reached in the container the member will break, the fold being straightened out by the pressure in the container. However, the member can also be elastic to indicate on a non-elastic scale the elongation when the member is being stretched. The alarm or more correctly the indication obtained by means of such a device is not suited, however, to give alarm e.g. when a stomi bag has been filled too much during the sleep or when the bag is not kept under direct visual observation.

EP-A-130670 relates to an apparatus for sensing fluid pressure within a fluid delivery pipe, including a strain gauge device.

SUMMARY OF THE INVENTION

According to the invention in order to overcome the problems discussed above the stomi bag has obtained the characterizing features of claim 1.

BRIEF DESCRIPTION OF THE DRAWINGS

In order to explain the invention in more detail reference is made to the accompanying drawings in which.

DESCRIPTION OF THE PREFERRED EMBODIMENTS

Figure 1:
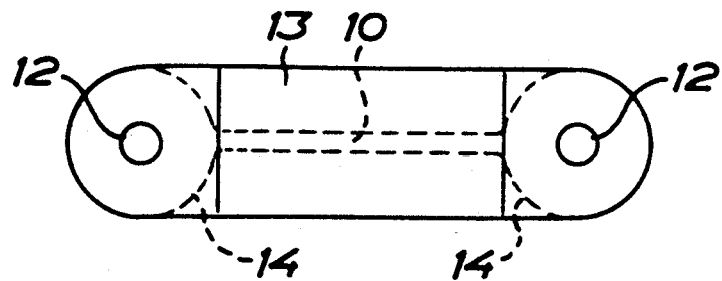
FIG. 1 is a plan view of a sensor forming part of the device of the invention.
Figure 2:
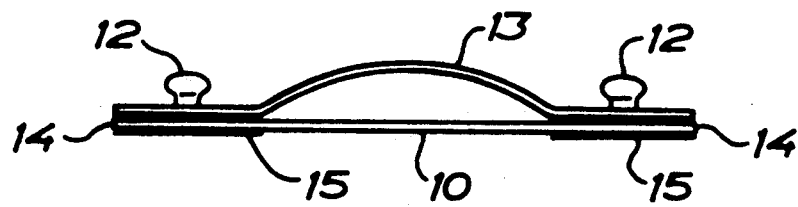
FIG. 2 is a side view of the sensor in an unactivated condition.
Figure 3:
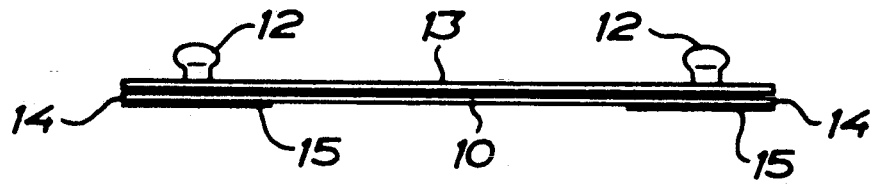
FIG. 3 is a corresponding side view of the sensor in an activated condition.
Figure 4:
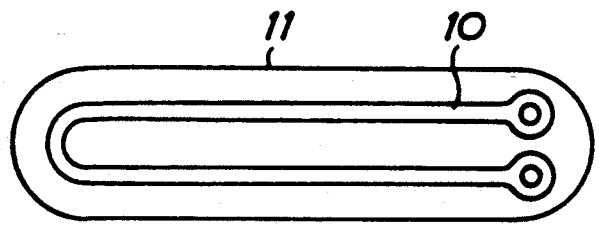
FIG. 4 is a plan view of a strip of elastic foil having an elastic resistance element connected therewith, which can form part of the sensor.

The sensor of FIG. 1 to 3 comprises a strip 10 which can consist of an elastomer (e.g. silicon rubber) having carbon powder admixed thereto in order to form as such an electric resistance element, or according to FIG. 4 can consist of a stretchable foil 11 having an electric resistance element 10 attached thereon or embedded therein, said element being of the mentioned construction, elastomer with carbon powder. The resistance element 10 has an electric resistance which changes by elastic stretching of the element. At the ends thereof the resistance element is connected with electric contacts 12, which are fixed to the ends of a flexible but non-elastic band 13 having a shorter length than the strip 10 so that the sensor, when left on its own, will be in the condition which is shown in FIG. 2, i.e. the band 13 forms an arch over the retracted (not stretched) strip 10. On the lower side of the strip 10 there is applied at the ends of the strip where the strip is widened to form circular plates 14, self-adhering glue 15 preferably covered by protection tape.

Figure 5:
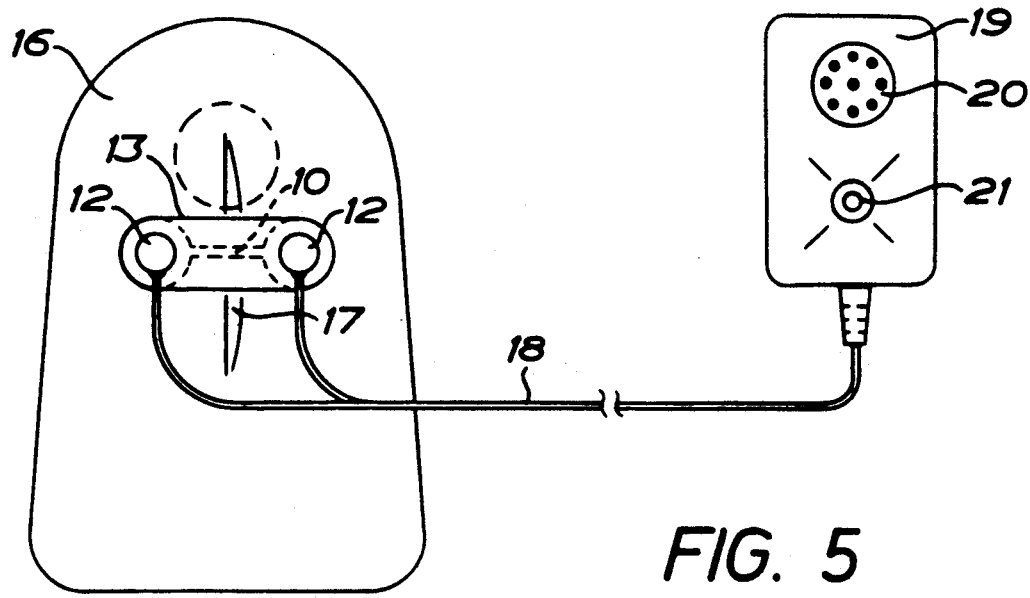
FIG. 5 is a side view of a container having a sensor mounted thereon, which is connected to an alarm device.

The strip 10 or the resistance element 10 attached thereto can be stretched as much as is allowed by the non-elastic band 13 so that the sensor will be in the condition according to FIG. 3, and in this condition wherein the resistance element has an elongation determined by the band 13, and thus an electric resistance of a predetermined value, the sensor can be attached to a stomi container 16, FIG. 5, which consists of a flexible plastic bag. When the sensor has been attached and it is released, it will return to the condition according to FIG. 2, a single fold or a folded or wrinkled portion 17 of the wall of the stomi bag being formed. A conduit 18 is connected to the contacts 12 in order to connect the sensor with an alarm box 19 which has an acoustic or visual alarm means 20 and 21, respectively. The alarm box can be provided with means replacing or supplementing said alarm means, which give an alarm in the form of a vibration which is directed from the alarm box towards the skin of the stomi patient. In the alarm box there are provided electric circuits which activate these alarm means when the resistance of the sensor element has a predetermined value preferably corresponding to the resistance value mentioned above, when the band 13 is extended.

When the stomi bag is being filled the wall thereof will be exposed to an increasing internal pressure as the level increases, and then the fold or the folded portion will be extended the resistance element 10 at the same time being stretched and the resistance thereof then being changed. When the stomi bag is nearly full the resistance should have said predetermined value in order that the alarm box gives an alarm so that the attention of the carrier of the stomi bag is drawn to the fact that it is time for changing the bag. The alarm box can be arranged for mounting at a suitable position on the body of the stomi patient under the clothes or at a suitable position in or on a garment.

It is not necessary that the stomi bag has a fold or a folded or wrinkled portion in case the material from which the stomi bag is made as such can be stretched or extended.

Figure 6:
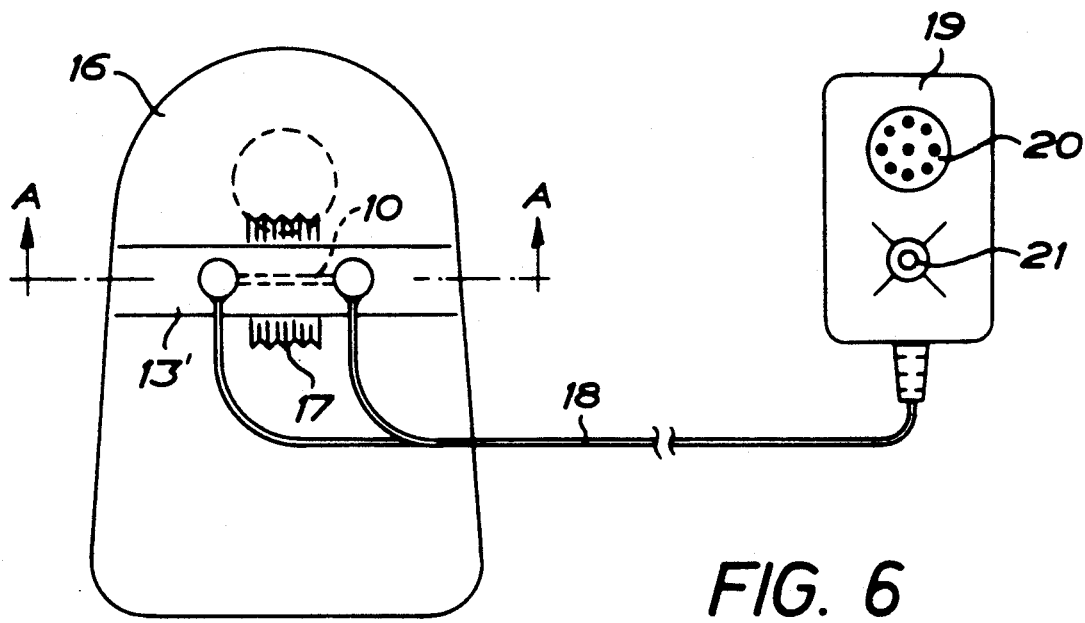
FIG. 6 is a side view similar to that of FIG. 5 of an embodiment wherein the sensor is integrated with the container.
Figure 7:
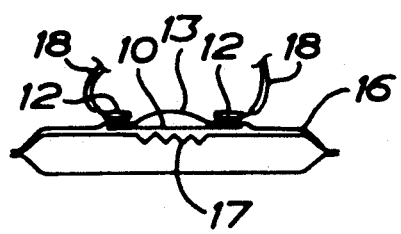
FIG. 7 is a fragmentary cross-sectional view, taken along line A—A in FIG. 6.

In the embodiment described it is necessary for the stomi patient himself to attach the sensor to a stomi bag of standard type. In FIGS. 6 and 7 the sensor is permanently attached to the stomi bag to be delivered together with the bag from the manufacturer thereof. For example, the resistance element 10 as shown in FIGS. 6 and 7 can be attached directly to the bag wall at the ends thereof over the folded or extensible portion 17. Then, the contacts 12 can be imbedded between the bag wall and an outer layer 13' on said wall by fusion, said outer layer replacing the band 13 in the embodiment according to FIGS. 1 to 5. The resistance element is located between the layer 13' and the container wall or integrated with the container wall in another manner, the resistance element being located, on or in the container wall. The only thing that the user has to do in this case is to connect the alarm box to the stomi bag.

I claim:

1. Stomi bag, characterized in that for monitoring the level of material collected in the stomi bag an elastic resistance element (10) is fixedly connected to the bag wall at the ends thereof to span an extensible portion (17) of the bag wall, said element having an electric resistance changing by stretching of the element, means being provided for connecting the element to an alarm means (19) reacting to resistance change of the resistance element due to extension of said portion of the bag wall by pressure against the bag wall at predetermined level of material collected in the stomi bag.

2. Stomi bag as in claim 1 wherein the resistance element (10) is arranged in or on a stretchable foil (11).

3. Stomi bag as in claim 1 or 2 wherein the resistance element (10) or the foil (11) has a self-adhering coating (15) for attachment to the stomi bag (16).

4. Stomi bag as in claim 1 wherein the extensible portion comprises a fold or a folded or wrinkled portion of the bag wall.

5. Stomi bag as in claim 1 wherein the resistance element (10) is integrated with the bag wall.

* * * * *